(12) United States Patent
Brady et al.

(10) Patent No.: US 12,225,906 B1
(45) Date of Patent: Feb. 18, 2025

(54) PATHOGENIC AFFINITY PATHWAY OF INFECTIOUS OR PARASITIC ORGANISMS FOR NANOGRAM AND PICOGRAM DOSIMETRY PROPHYLAXIS OR CURE

(71) Applicants: Terry Earl Brady, The Valley (AI); Anthony Lee Dellinger, Burlington, NC (US); Lowell Hughes, The Valley (AI); Melinda K. M. Goddard, The Valley (AI); Christopher E. Starr, New York, NY (US); Abed Alqader Ibrahim, Greensboro, NC (US)

(72) Inventors: Terry Earl Brady, The Valley (AI); Anthony Lee Dellinger, Burlington, NC (US); Lowell Hughes, The Valley (AI); Melinda K. M. Goddard, The Valley (AI); Christopher E. Starr, New York, NY (US); Abed Alqader Ibrahim, Greensboro, NC (US)

(*) Notice: Subject to any disclaimer, the term of this patent is extended or adjusted under 35 U.S.C. 154(b) by 0 days.

(21) Appl. No.: 18/897,019

(22) Filed: Sep. 26, 2024

(51) Int. Cl.
| | | |
|---|---|---|
| A61K 9/50 | (2006.01) | |
| A01N 25/10 | (2006.01) | |
| A01N 59/00 | (2006.01) | |
| A01N 59/16 | (2006.01) | |
| A01P 1/00 | (2006.01) | |
| B82Y 5/00 | (2011.01) | |

(52) U.S. Cl.
CPC ............. *A01N 59/16* (2013.01); *A01N 25/10* (2013.01); *A01N 59/00* (2013.01); *A01P 1/00* (2021.08); *A61K 9/5036* (2013.01); *B82Y 5/00* (2013.01)

(58) Field of Classification Search
CPC ... A61K 9/5015; A61K 9/5036; A61K 9/5052
See application file for complete search history.

(56) References Cited

U.S. PATENT DOCUMENTS

| | | | |
|---|---|---|---|
| 5,848,975 A | 12/1998 | Phillips | |
| 9,302,012 B2 | 4/2016 | Miller | |
| 2004/0047979 A1* | 3/2004 | Qiu | G02B 1/043 427/2.1 |
| 2012/0239140 A1* | 9/2012 | Wittchow | A61L 31/16 623/1.46 |
| 2016/0059605 A1* | 3/2016 | Schmidt | B41M 5/502 156/60 |
| 2022/0105047 A1* | 4/2022 | Jeong | A61K 35/28 |

FOREIGN PATENT DOCUMENTS

| | | | |
|---|---|---|---|
| CN | 116808302 A | * | 9/2023 |
| WO | 2010050468 A1 | | 5/2010 |
| WO | 2011136268 A1 | | 11/2011 |
| WO | 2012134184 A2 | | 10/2012 |
| WO | 2012147773 A1 | | 11/2012 |

OTHER PUBLICATIONS

Acevedo-Fani et al. Food Biophysics, 2017, 12, 299-308.*

* cited by examiner

*Primary Examiner* — Kyle A Purdy

(57) ABSTRACT

The sustenance of life is driven by recognition of and access to energy sources. This process has remained unchanged over billions of years, guiding cellular nutrition through molecular recognition, akin to the food pyramid. At the atomic or nanoscale, chemotaxis enables organisms to identify ingestible matter and is driven by their need for fuel, rather than from the sustenance itself. Chemotaxis, one of nature's most potent yet invisible organic forces, operates independently of molecular charge dynamics to locate and identify microscopic sustenance. Infectious organisms, such as pathogenic microbes and parasites, depend on chemotactic pathways to locate nutrition across all scales. This invention leverages this phenomenon by "baiting" these pathways with nutritive matter that encapsulates biocidal agents that are harmless to humans but lethal to infectious organisms once ingested. These nutritive biocidal agents could be employed as topical, oral, injectable, or aerosolized formulations, as well as hydrogel or slow-release implants.

16 Claims, 1 Drawing Sheet

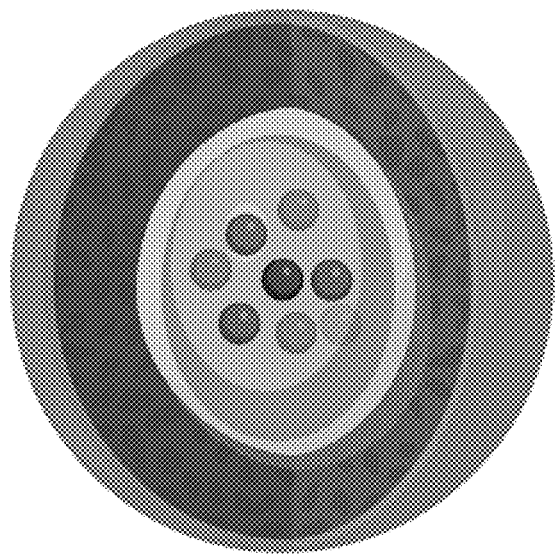

PATHOGENIC AFFINITY PATHWAY OF INFECTIOUS OR PARASITIC ORGANISMS FOR NANOGRAM AND PICOGRAM DOSIMETRY PROPHYLAXIS OR CURE

FIELD OF THE INVENTION

This invention describes a dual-action formulation that targets and eradicates pathogens (microorganisms) via a biocidal agent (toxin) and a nutritive component (food or fuel source). The nutritive component is formulated to stimulate chemotaxis in pathogens, such as bacteria, fungi, and viruses, attracting them into proximity to facilitate ingestion of a toxin encapsulated in the nutritive matrix. Thus, the invention serves as an attractant and delivery mechanism for chemotactic, endogenous eradication of pathogens.

BACKGROUND OF THE INVENTION

Pathogens have posed threats to humans for millennia by causing a wide range of diseases. Of these, bacterial and viral maladies are among the most prevalent due to their ease of transmission. Bacteria are complex, relatively large cellular organisms that ingest nutrients to perform essential metabolic functions, including mitosis—as independent microbes, or interacting with a host. In contrast, viruses consist only of genetic material (DNA or RNA) encased in protein and some with lipid envelopes. In addressing the infectious diseases caused by such pathogens, therapeutic methods have also faced limitations due to the emergence of resistance, as organisms can rapidly adapt to evade single-target approaches.

Beyond bacteria and viruses, other eukaryotic pathogens such as fungi, protozoa, and metazoan parasites pose significant dangers to humans. By example, *Ascaris lumbricoides*, a parasitic roundworm, is considered one of the most widespread infectious diseases globally, currently affecting approximately one billion people. This parasite targets the human gut, making it a public health concern in many regions. Such pathogens employ unique mechanisms to induce disease, complicating the understanding of the biology of infection. Nonetheless, consistent patterns of pathogenesis between infectious agents and their hosts can be identified.

Pathogens are remarkably diverse, including differences in size, shape, and composition (e.g., DNA versus RNA, presence of an envelope) between and within classes. These organisms vary from submicron virions to multicellular parasites. Viruses, the smallest pathogens, range from 20 to 300 nanometers, allowing them to pass through most biological barriers and evade immune detection. Bacteria are generally larger, ranging from 0.5 to 5 microns, with some reaching up to 10 microns. Fungi, such as yeasts, vary from 3 to 40 microns, while molds and other species of fungi can grow significantly larger. Some parasites range from 10 to 100 microns, depending on their life stage and environment, whereas ectoparasites and parasitic worms can range from millimeters to centimeters.

Irrespective of host dependence, bacteria, fungi, and parasites are capable of DNA replication, transcription, translation, and energy production. Viruses, by contrast, carry only essential genetic information in the form of nucleic acids. Unlike cellular organisms, viruses rely on the host cell to package, preserve and replicate virions.

*Demodex* mites are microscopic ectoparasites that inhabit human hair follicles and sebaceous glands, particularly on the face and eyelashes. Two species, *Demodex folliculorum* and *Demodex brevis*, most commonly affect humans. *Demodex* mites are generally not visible to the naked eye and may go unnoticed in small numbers. However, in individuals with weakened immune systems, they can cause a variety of dermatological and ocular conditions, such as demodicosis, rosacea, dry eye disease, blepharitis and recurrent chalazia. *Demodex* proliferation often leads to symptoms like itching, redness, inflammation, and scaling of the skin, particularly around the eyelids. They feed on sebum and cellular debris. Although *Demodex* mites are not known to transmit diseases, their presence can exacerbate skin and eye conditions, complicating treatment and management. Increased bacterial loads of Gram-positive bacteria are seen with *Demodex* blepharitis and are believed to increase the risk of catastrophic endophthalmitis infections following eye surgery. Effective control can nonetheless be challenging due to their microscopic size, widespread distribution, and the need for targeted treatments that minimize irritation to sensitive areas, such as ocular tissues.

Another familiar example of ectoparasites is the Phthiraptera, or lice. These are parasitic insects that typically infest the hair and scalp, where they feed on microscopic amounts of blood. When present, itching and discomfort can lead to secondary infections due to scratching. Head lice are the most common, particularly among school children, as they can spread rapidly through close contact, making infestations difficult to control. Notably, lice do not transmit bloodborne diseases, making them primarily a nuisance.

Developing effective treatments for pathogenic fungi and parasites nonetheless remains a global challenge due to their eukaryotic nature, which complicates the identification of therapeutic targets that are not shared with the host. Antifungal and antiparasitic drugs, therefore, tend to be less effective and more toxic than antibiotics, and pathogens with varying life cycles add further complexity. For example, protozoan parasites like *Plasmodium* species, which cause malaria, have complex life cycles involving multiple hosts and various stages, each of which may require specific therapeutic interventions to achieve complete eradication. Malaria, the most common protozoal disease, affects 200-300 million people yearly, with 1-3 million deaths. Caused by four *Plasmodium* species, transmitted by *Anopheles* mosquitoes, *Plasmodium falciparum* (the most studied) has eight life stages, requiring both human and mosquito hosts. Gametes form in humans but fuse into a zygote only in the mosquito's gut, with specific stages targeting the insect gut, human liver, and red blood cells.

Given their diversity and adaptive mechanisms, achieving effective and comprehensive pathogen control thus remains an ongoing challenge. Many antimicrobial strategies focus on directly targeting their replication or survival mechanisms. However, these approaches often face limitations due to the development of resistance, side effects, and incomplete eradication. Therefore, there is a need for innovative approaches that enhance the delivery and effectiveness of biocidal agents while minimizing resistance and collateral damage to host tissues.

Traditional uptake mechanisms, like passive diffusion, allow for small, non-polar molecules to cross the bacterial cell membrane without energy expenditure. Other mechanisms, such as facilitated diffusion, involve specific transport proteins that help larger or polar molecules enter the cell. Nutrients such as ions, sugars, and amino acids are moved against their concentration gradients through active transport mechanisms and require energy. Additional mechanisms include group translocation, which involves the chemical modification of a molecule during transport.

In bacteria, specialized systems like the phosphotransferase system (PTS) actively transport glucose into the cell. Another example is the use of siderophores, which are molecules secreted by bacteria to bind and transport iron. Some antibiotics, such as cefiderocol, exploit this system by being conjugated with a siderophore, facilitating their uptake into the bacterial cell through the siderophore-iron transport mechanism. This approach takes advantage of innate nutrient acquisition pathways, effectively transferring the antibiotic into the cell along with the nutrient. This method can increase the concentration of the toxin inside the bacteria, enhancing its antimicrobial efficacy. The system also includes components that are broken down by bacterial enzymes, releasing the biocidal agent in a form readily absorbed by the bacteria.

In viruses, SARS-CoV-2, by example, demonstrates a high affinity for the ACE2 receptor on host cells. This affinity-based binding highlights a broader principle: viruses and other pathogens do not consume or metabolize but instead rely on specific interactions for attachment and replication. By mimicking such high-affinity interactions in the delivery system, it is possible to effectively bring pathogens into proximity with biocidal agents, ensuring their eradication upon contact.

Another essential aspect of pathogen survival and proliferation is the capability to locate and acquire nutrients. The behavior of nearly every organism is often guided by chemotaxis, a process through which they detect and move relative to chemical stimuli, such as nutrients, while avoiding harmful substances. Chemotaxis thus drives many pathogenic bacteria to navigate toward nutrient-rich environments within the host, concentrating in bodily tissues or the bloodstream for their growth, replication, and pathogenicity. While some organisms can make their own food, convert energy through photosynthesis, or consume organic materials from a host source, "nutrient"/fuel acquisition is a universal requirement across all classes of pathogens, including bacteria, viruses, fungi, protozoa, and parasites.

Understanding how pathogens detect and move toward nutrients can therefore inform strategies to intercept these processes for therapeutic and prophylactic intervention. Specifically, chemotactic biology creates an opportunity to design antimicrobial delivery systems that mimic nutrient signals as pathogen attractants. The present invention would thus draw pathogens toward and enhance direct uptake of biocidal agents to achieve endogenous eradication. Precision targeting could also mitigate the impact on healthy tissues and cells, and thus, potential side effects from specific antimicrobials.

Chemotaxis is also notably distinct from conjugation and coincidental uptake mechanisms. U.S. Pat. No. 9,302,012 B2, titled Anti-Bacterial Siderophore-Aminopenicillin Conjugates, describes the use of synthetic siderophores conjugated with aminopenicillins to exploit bacterial iron uptake. This method enhances the delivery of antibiotics like ampicillin and amoxicillin into Gram-negative bacteria by overcoming membrane impermeability, particularly in resistant strains. This "piggybacking" strategy leverages cellular pathways, such as the phosphotransferase system (PTS), or iron transport mechanisms. Additional patents, including WO2010/050468, WO2011/136268, WO2012/134184, and WO2012/147773, describe similar strategies for conjugating cephalosporins with siderophores to achieve antibiotic delivery. However, unlike siderophore-mediated approaches that rely on bacterial iron acquisition, the proposed invention introduces a system that attracts not only bacteria, but also, fungi, protozoa, viruses, and other pathogens, and stimulates ingestion of the biocidal agent embedded in a nutrient matrix. This approach thus distinguishes itself from the opportunistic siderophore-based methods by leveraging the innate nutrient-seeking biology of a range of pathogens across multiple classes.

In the context of the urea breath test (UBT) for *Helicobacter pylori* (*H. pylori*) diagnosis, administering a radiolabeled urea alongside a nutrient source has shown potential to improve test sensitivity. The traditional method described in U.S. Pat. No. 5,848,975 teaches dissolving urea in water, but studies have suggested that adding nutrient-rich suspensions, such as pudding or yogurt, can enhance the interaction between urea and *H. pylori*. By doing so, it is hypothesized that the bacterial metabolic activity is nourished, allowing for more robust urea hydrolysis, more efficient urease production and urea breakdown. This results in an increased release of labeled carbon dioxide ($CO_2$), which is detectable in breath samples. In one aspect, the intent of this approach is to slow gastric emptying to increase the duration of urea contact with *H. pylori*. One example is the role of citric acid in UBT, which optimizes the pH environment and delays gastric emptying. However, adding a nutrient source suggests enhanced bacterial metabolism by providing additional energy substrates. *H. pylori* primarily metabolize amino acids and lipids within the stomach environment for energy, and by providing these alongside the urea, the bacterial activity can be sustained, leading to more reliable test results. Notably, this patent, as well as the industry practice of administering the diagnostic reagents in substrates palatable to both the patient and target pathogens, teaches utility only for diagnostic detection of microbial colonization, rather than endogenous eradication after ingestion of a chemoattractant biocidal formulation.

In U.S. Pat. No. 10,278,927 B2, Layer-by-Layer (LbL) assembly technique has been used to construct a stable nano system for drug delivery, specifically therapeutic agents such as doxorubicin. The patent teaches the coating of particles coated with LbL thin films that contain therapeutic agent(s) in the layers. The invention uses LbL assembly to provide a stable nanoparticle that comprises a negatively charged liposomal core that may contain a first therapeutic agent, followed by four layers composed of poly-L-arginine (PLA), siRNA therapeutic agent, PLA, and hyaluronic acid (HA). While establishing a stable system with a diameter of less than 1,000 nm, the patent provides a carrier for therapeutic agents such as doxorubicin for cancer treatment, but it does not teach the use of nutrient attractants to target infectious agents through chemotaxis.

However, several economic and scalable techniques have been used to perform LbL assembly for various applications. Layer-by-Layer (LbL) assembly was initially carried out through the sequential adsorption of oppositely charged materials onto a substrate, guided by enthalpic and entropic forces. The technique's versatility quickly expanded, resulting in a potential for incorporating a range of molecular interactions in the assembly process. This approach allows for precise control over the thickness, composition, as well as functionality of each layer, making it ideal for the development of complex systems.

The Layer-by-Layer (LbL) assembly technique also provides control and versatility in coating substrates with materials such as polymers, colloids, biomolecules, and cells. Compared to other thin-film deposition methods, LbL allows for precise manipulation of layer thickness and composition, which is essential for constructing the proposed biocidal delivery system. Moreover, this customization is critical for ensuring that each layer enhances chemotaxis, mimics nutrients, and controls the release of the biocidal agent, making LbL a suitable option for such an application.

Spraying techniques have also been applied to various aspects of Layer-by-Layer (LbL) film assembly, from drying aligned films to coating substrates with multilayer structures. This method uses fine aerosols to deposit each layer onto the nanoparticle surface by spraying solutions of oppositely charged materials, followed by rinsing to remove excess material. Compared to dipping techniques, spray deposition offers faster layer application and is well-suited for large-scale production and continuous coating processes.

By engineering chemotactic attraction into a multi-faceted biocidal delivery system and optimizing LbL techniques, the proposed invention presents an adaptable strategy capable of targeting a broad spectrum of pathogens. This approach is advantageous for addressing the complexity of polymicrobial infections, biofilms, and resistant strains that represent significant challenges in clinical settings.

SUMMARY OF THE INVENTION

The invention represents a novel platform that combines a chemoattractant, nutritive component with an encapsulated biocidal agent or agents to leverage the essential need for nutrients and chemotaxis, or the attractant and uptake mechanisms, pathogens evolved to obtain them. Mimicking these innate processes thus enables a biocidal agent to be absorbed along with nutrients and allows for endogenous antimicrobial delivery. The inclusion of diverse toxic agents may further confer broad-spectrum capabilities to mitigate risks for resistance and ensure thorough eradication.

In this invention, the biocidal and nourishing formulation is implemented through Layer-by-Layer (LbL) assembly. This method allows for the strategic construction of nanoparticles, where the outer shell is designed to be attractive and consumable by the target microorganisms for administration consistent with fuel or nutrients and to therefore elude innate defenses. Once the pathogen ingests the nanoparticle, it would break down the shell, thereby exposing the core containing the antibiotic and/or biocidal agent. This novel delivery approach ensures that the pathogens are directly exposed to the active agent to optimize efficacy of the treatment by targeting the microorganisms precisely where and when they are most susceptible to eradication.

The proposed formulation is designed with a nanometer-scale range that provides compatibility across various pathogenic organisms, including bacteria, fungi, viruses, protozoa, and parasites. With a typical size distribution between 100-300 nanometers, the nanoparticles are small enough to be readily ingested by bacteria and fungi, which generally have cellular dimensions in the micron range and are capable of internalizing nanoparticles below 300 nm through natural ingestion pathways such as endocytosis or phagocytosis. Similarly, larger parasites are also capable of engulfing nanoparticles of this size. Viruses, although much smaller (ranging from 20 to 300 nanometers), can also interact with the delivery system through adsorption or endocytosis when attached to host cells. This adaptable size ensures effective delivery to both unicellular pathogens and complex microorganisms without significant modifications, creating a platform for biocidal applications across a range of infectious agents. As such, embodiments could include but not be limited to topical, oral, aerosol, injectable and infusion formulations for a corresponding range of applications.

However, the primary embodiment would comprise a nanoparticle size below 300 nanometers specifically optimized for targeting pathogens, such as bacteria, fungi, protozoa, and viruses, ensuring they can be ingested or interact with natural pathways. This size range would allow for delivery of toxins capable of penetrating biofilms and breaching cellular and organism barriers, offering broad-spectrum compatibility.

BRIEF DESCRIPTION OF THE DRAWINGS

FIG. 1 is a molecular representation of an exemplary nanoparticle synthesized through a Layer-by-Layer (LbL) assembly technique. The system comprises a polydopamine-coated core, followed by sequential layers: a first layer of chitosan, a second layer consisting of dextran and glucose, a third layer of alginate integrated with lipids, and an outermost layer of keratin integrated with agar.

DETAILED DESCRIPTION OF THE INVENTION

The proposed invention introduces a novel approach to endogenous eradication of pathogenic microorganisms by using a highly specialized, multilayered nanoparticle that mimics nutrient uptake stimulants. By constructing nanoparticles that are engineered to attract pathogens and deliver nutrients, the invention ensures that biocidal agents are delivered precisely. This formulation can thus enhance the effectiveness of toxic agents as well as reduce potential side effects by selectively targeting pathogens.

Specifically, the invention incorporates nutrients or analogs that introduce a toxic agent or an array of agents into the cells through nutritional pathways stimulated by chemotactic cues. This process is analogous to the co-transport of sodium and glucose or amino acids in the kidneys and conjugation of a therapeutic with glucose or a glucose analog, allowing for the drug to be transported into the bacterial cell via the transport system used for glucose. However, the initiation of the process is targeted, rather than coincidental.

In the primary embodiment of the present invention, the Layer-by-Layer (LbL) assembly technique is employed to construct a complex, multi-layered nanoparticle system designed for targeted delivery of biocidal agents to pathogenic microorganisms. This invention is engineered to exploit the innate nutrient-seeking behaviors of pathogens, ensuring that the nanoparticles are recognized, ingested, and endogenously deliver biocidal agents directly to the targeted organism. Each layer of the system is designed to balance biocompatibility, stability, and efficacy, with specific compounds selected to enhance pathogen chemotaxis and controlled antimicrobial release.

In this invention, Spin-Spraying Assembly is used to provide fast deposition, large-scale production and continuous coating processes as well as providing excellent thin and uniform layers. Spin-Spraying Assembly stands out as an automated, cost-effective and scalable method compared to other deposition techniques. It offers lower equipment and energy costs by using basic equipment that consumes less energy. It also ensures thin and uniform coatings with efficient material usage, reducing waste and further lowering costs. The method's scalability also allows for affordable mass production and continuous coating process applications.

The first layer applied to the core is composed of chitosan, a naturally occurring polymer known for its biocompatibility and antimicrobial properties. This layer ranges between 10-25 nm in thickness and contributes to the overall positive charge of the system, further enhancing its attraction to bacterial cells. The second layer is designed to mimic the natural food sources of pathogens and is composed of dextran combined with chemotactic compounds such as glucose. These substances are metabolized by pathogens, making the nanoparticle appear as a nutrient-rich attractant, thereby encouraging ingestion.

The thickness of the second layer is between 20-25 nm and mimics a nutrient-rich environment, stimulating the pathogen to respond the nano delivery system as a natural food source to stimulate toxin ingestion or adsorption. The third layer comprises alginate integrated with lipids, such as dried fat or milled cornstarch. This layer is approximately 25-50 nm in thickness and serves multiple functions where it protects the underlying layers during transport to the target site, ensuring stability in various environments. It further provides a controlled release mechanism of action, allowing the silver ions to be gradually released once the nano delivery system is ingested by the pathogen. The lipid component enhances the attraction of the encapsulated toxin by mimicking natural food sources, further promoting pathogen ingestion.

The outermost layer comprises proteins, such as keratin, that are integrated with specific culture media components, such as those in conventional agars. This layer has a thickness less than 25 nm and is designed to stabilize the formulation in varying environmental conditions as well as provides a secondary chemotactic signal, further ensuring that the nano delivery system is ingested by the target pathogen. The total particle size would be <300 nm, which may be readily ingested by pathogens since the largest particles that bacteria can ingest are generally a few micrometers in diameter.

In this invention, optimal LbL assembly is crucial for ensuring effective layer deposition and system performance. Several factors have been taken into consideration including the pH of the solutions, which plays a significant role, particularly when working with materials such as chitosan, alginate, and polydopamine. An optimal pH range of 4.5 to 7.5 is used, since it ensures that the materials (e.g., chitosan) retain their positive charge. This allows for effective interaction with negatively charged layers, as well as providing flexibility in several forms for targeting numerous infectious agents. Temperature is another important factor, with an ideal range of room temperature between 20° C. and 40° C. to facilitate efficient adsorption and binding of the layers without compromising stability of the nanoparticle core. Additionally, the concentration of each layer component typically falls between 0.1 and 1 mg/mL to ensure proper coating without excessive buildup. The binding time for layer deposition ranges from 5 to 30 minutes, depending on the materials and the layer thickness.

In one exemplary embodiment of the present invention: The core of the formulation comprises a polydopamine (PDA)-coated toxin, such as nanoparticles, antibiotic, antifungal, and/or antiparasitic between 100-150 nm in size. The encapsulated nanoparticles include but are not limited to silver nanoparticles. The inclusion of nanoparticles, like silver, can provide potent antimicrobial properties, while the PDA coating adds an extra layer of biocompatibility and reduces cytotoxicity. The positively charged surface of the core is particularly attractive to bacteria, given their negatively charged cell walls. Additionally, PDA would serve as a platform for the LbL assembly and offer antimicrobial activity, particularly against *Staphylococcus aureus*. The PDA layer is also biodegradable, ensuring that it breaks down safely after delivering the biocidal agent.

Subsequently, alternative chemoattractant elements are incorporated into the layers of the nanoparticle formulation to enhance the attraction and ingestion by a broader range of pathogens. The chemoattractant elements may include a diverse range of molecules that are recognized as nutrients or energy sources by different organisms, optimizing the formulation for specific applications or environments. As such, amino acids, peptides, and specific sugars could be included in different layers to attract pathogens like bacteria, fungi, and protozoa that respond to these signals. Examples of sugars and carbohydrates include cellobiose, fructose, galactose, glucose, maltose, mannose, ribose, sucrose, and xylose. Amino acids and peptides that could be used include cysteine, folic acid derivatives, histidine, L-arginine, L-asparagine, L-glutamine, L-leucine, L-serine, and lysine-rich peptides. Lipids and fatty acids such as arachidonic acid, linoleic acid, oleic acid, palmitic acid, phosphatidylcholine, and phosphatidylserine may also be incorporated. Additionally, vitamins and cofactors like biotin, folic acid, nicotinic acid, riboflavin, thiamine, and vitamin B12 (cobalamin) can be used. Other chemosensory molecules, including nucleotides (e.g., ATP, ADP), quorum sensing molecules (e.g., AHLs—acyl-homoserine lactones), siderophores (e.g., *Enterobacter*, pyochelin), iron-binding proteins, and methylglyoxal, may also be employed to enhance the attraction of various pathogens or organisms. The addition of these diverse chemoattractant elements ensures that the nanoparticles can effectively attract a range of pathogens by stimulating their innate chemotactic responses.

Furthermore, the core of the nanoparticle could be adapted to include different materials or combinations of materials that serve as biocidal agents, antiparasitic, antifungal, or other broad-spectrum antimicrobials. Depending on the target organism, various nanoparticles, such as metal-based or polymeric nanoparticles, can be used to enhance efficacy. For example, gold, zinc oxide, and titanium dioxide nanoparticles can provide additional mechanisms of action against pathogens through oxidative stress, metal ion release, and photocatalytic activity. Moreover, the core materials can be combined with specific drugs, antibiotics, or antifungal agents to create a synergistic effect, increasing efficacy while minimizing resistant mutations. Examples of suitable nanoparticles include silver, gold, zinc oxide, titanium dioxide, copper oxide, and iron oxide nanoparticles, quantum dots (e.g., CdTe, CdSe), halogen-functionalized fullerenes, halogenated fullerenes, and carbon nanotubes. Antimicrobial agents and antibiotics can include but not be limited to amoxicillin, cefiderocol, ciprofloxacin, daptomycin, gentamicin, metronidazole, tetracycline, tobramycin, and vancomycin. For antifungal applications, agents such as amphotericin B, caspofungin, fluconazole, itraconazole, nystatin, terbinafine, and voriconazole may be utilized. Antiparasitic agents like albendazole, artemisinin, ivermectin, metronidazole, miltefosine, moxidectin, nitazoxanide, and praziquantel can also be incorporated. Other biocidal agents, such as benzalkonium chloride, chlorhexidine, *eucalyptus* oil, hydrogen peroxide, phenolic compounds, sodium hypochlorite, and thymol may also be included for broad spectrum efficacy. Additionally, combination agents such as polydopamine (PDA)-coated silver nanoparticles combined with antibiotics (e.g., tobramycin), lipid-coated zinc oxide nanoparticles with antifungals (e.g., amphotericin B), and layered composites with iron oxide and ciprofloxacin can provide enhanced activity and targeted delivery against respective pathogens.

The flexible delivery and design of the invention thus allows it to be tailored to various embodiments, making it versatile for treating a broad spectrum of pathogens. As a primary application, topical formulations can include creams, ointments, gels, lotions, or shampoos that are applied directly to the skin, scalp, or eyelashes. In one formulation, the delivery system in this embodiment would be optimized to mimic natural skin secretions for *Demodex* mites in the treatment of blepharitis, or, in the case of ectoparasites, specific bloodstream nutrients, to attract target pathogens. Upon contact or ingestion by the parasites or pathogens, the antimicrobial agents would be released, effectively neutralizing them. Topical formulations provide a localized effect, limiting exposure and thus, potential side effects.

For gastrointestinal infections caused by pathogens, such as *Ascaris lumbricoides* or other intestinal parasites, bacteria, or fungi, an oral application can be administered for esophageal or gastric infections, as well as incorporated into enterically coated and time-released tablets, capsules, or a liquid suspension designed to withstand the acidic environment of the stomach, or to release the chemoattractant agents and biocides in the intestine, wherever the target pathogens are present.

For respiratory infections caused by airborne bacterial, fungal, or viral pathogens, another aerosol or inhalable application could be formulated and administered through nebulizers or inhalers for both acute and chronic conditions, such as pneumonia, tuberculosis, or bronchitis. For example, an aerosolized formulation comprising nanoparticles with a core of halogen-functionalized fullerenes and outer layers containing chemotactic attractants could be developed for treating fungal or bacterial lung infections.

In cases of systemic and localized tissue infections, another application can be prepared as a sterile injectable solution. Administered intravenously, intramuscularly, or subcutaneously, the delivery system could circulate through the bloodstream directly or through tissue infusion, formulated for chemotactic stimulation of targeted species. Upon uptake of the nutrient-mimicking components by the infectious organisms, the release of the biocidal agents would thus provide endogenous eradication.

For long-term protection or localized deep-tissue infections, another application can be embedded in hydrogels, transdermal patches, or slow-release implants for a continuous, controlled release of chemotactic signals and biocidal agents. These formulations can be used in surgical sites, chronic wound management, catheters, or as part of implantable devices to provide prophylactic prevention or treatment of biofilm-associated infections. A hydrogel composition can also be used to prevent biofilm formation on wounds or implanted devices. Hydrogels can adapt to the shape of the application site, ensuring consistent biocidal distribution in a moist environment conducive to healing.

For the purposes of this patent, the terms including but not limited to 'antibiotic,' 'biocidal,' 'microbiocidal,' 'toxin,' 'antifungal,' 'antiparasitic,' describe any agent capable of killing, neutralizing, inhibiting, or otherwise controlling the growth or activity of pathogens or microorganisms, including but not limited to bacteria, viruses, fungi, parasites, protozoa, spores, prions, algae, molds, yeasts, helminths, and any other pathogenic organisms that may pose risks to human, animal, or plant health, or contaminate various environments or materials.

What is claimed:

1. An antimicrobial and nutritive formulation for targeted neutralization of infectious agents, such as bacteria, fungi, viruses, protozoa, and ectoparasites, comprising:
   a. a core comprising a biocidal agent encapsulated within a polydopamine coating;
   b. sequential layers assembled on said core using a Layer-by-Layer (LbL) assembly technique, wherein each layer comprises a combination of biocompatible materials and chemotactic agents selected to attract specific pathogens;
   c. wherein the chemotactic agents mimic natural nutrient sources that stimulate chemotaxis in a targeted organism, wherein the organism is that of a bacteria, fungi, viruses, protozoa, or ectoparasites, thereby enhancing proximity to and ingestion of the biocidal agent;
   such that the sequential layers applied to the core comprise a first layer comprising chitosan with a thickness ranging between 10-25 nanometers, a second layer comprising dextran combined with a chemotactic compound comprising glucose with a thickness between 20-25 nanometers and a third layer comprising alginate integrated with lipids with a thickness between 25-50 nanometers.

2. The antimicrobial and nutritive formulation of claim 1, wherein the core is between 100-150 nanometers in size and comprises silver nanoparticles, halogen-functionalized fullerenes, or a combination thereof.

3. The antimicrobial and nutritive formulation of claim 1, wherein the formulation comprises an outermost layer comprising proteins integrated with specific culture media components, with a thickness less than 25 nanometers.

4. The antimicrobial and nutritive formulation of claim 1, wherein the biocidal agent comprises one or more antibiotic, antifungal, or antiparasitic agents, or a combination thereof.

5. A method for administering the formulation of claim 1, wherein the formulation is a topical, oral, injectable, or aerosol formulation, or embedded in a hydrogel or slow-release implant.

6. The antimicrobial and nutritive formulation of claim 1, wherein the formulation is formulated as a topical agent, such as a cream, ointment, gel, lotion, or shampoo.

7. The antimicrobial and nutritive formulation of claim 1, wherein the formulation is an aerosol or inhalable formulation.

8. The antimicrobial and nutritive formulation of claim 1, wherein the formulation is formulated as an oral tablet, capsule, gelcap, or liquid suspension.

9. The antimicrobial and nutritive formulation of claim 1, wherein the formulation is formulated as an injectable solution, wherein the antimicrobial and nutritive formulation circulates through the bloodstream, diffuses as an intramuscular or subcutaneous solution, or injected directly into or proximal to specific tissues.

10. The antimicrobial and nutritive formulation of claim 1, wherein the formulation is embedded in a hydrogel, a transdermal patch, or a slow-release implant to provide continuous, controlled release of chemotactic signals and biocidal agents.

11. The antimicrobial and nutritive formulation of claim 1, wherein the chemotactic agents are designed to attract specific pathogens based on their nutrient-seeking behavior, thereby targeting biofilm-associated infections and/or antibiotic-resistant strains.

12. The antimicrobial and nutritive formulation of claim 1, wherein the formulation is integrated into a medical device selected from the group consisting of wound dressing, catheters, or implantable devices.

13. The antimicrobial and nutritive formulation of claim 1, wherein the formulation allows for the incorporation of multiple biocidal agents and chemotactic components, enabling customized treatment for polymicrobial infections and/or complex infections involving multiple pathogen types.

14. The antimicrobial and nutritive formulation of claim 1, wherein the formulation leverages the innate nutrient acquisition pathways of pathogens to effectively deliver biocidal agents.

15. The antimicrobial and nutritive formulation of claim 1, wherein the LbL assembly technique is optimized for particle stability and controlled release of the biocidal agents, ensuring effective delivery to target pathogens.

16. The antimicrobial and nutritive formulation of claim 1, wherein the combination of the biocidal agent with the nutritive component enhances the targeted delivery and uptake by infectious agents, allowing for the use of significantly lower concentrations of the biocidal agent, thereby reducing potential toxicity to non-target cells and minimizing adverse effects.

\* \* \* \* \*